United States Patent [19]

Hettiarachchi et al.

[11] Patent Number: 5,602,888
[45] Date of Patent: Feb. 11, 1997

[54] RADIATION-INDUCED PALLADIUM DOPING OF METALS TO PROTECT AGAINST STRESS CORROSION CRACKING

[75] Inventors: Samson Hettiarachchi, Menlo Park; Thomas P. Diaz, San Martin; Gary P. Wozadlo, Los Gatos, all of Calif.

[73] Assignee: General Electric Company, Schenectady, N.Y.

[21] Appl. No.: 416,656

[22] Filed: Apr. 5, 1995

Related U.S. Application Data

[63] Continuation-in-part of Ser. No. 209,572, Mar. 10, 1994, which is a continuation-in-part of Ser. No. 143,513, Oct. 29, 1993, and a continuation-in-part of Ser. No. 143,514, Oct. 29, 1993, Pat. No. 5,448,605.

[51] Int. Cl.⁶ ..................................................... G21C 9/00
[52] U.S. Cl. ........................... 376/305; 376/306; 422/11; 422/14; 422/19
[58] Field of Search ..................... 376/301, 305, 376/306, 356, 357; 422/11, 14, 19

[56] References Cited

U.S. PATENT DOCUMENTS

| | | | |
|---|---|---|---|
| 3,023,085 | 2/1962 | McBride | 23/204 |
| 3,907,852 | 9/1975 | Oswald et al. | 260/448.2 |
| 4,093,559 | 6/1978 | Fernholz et al. | 252/443 |
| 4,111,830 | 9/1978 | Bannister | 422/17 |
| 4,579,751 | 4/1986 | Forster | 427/54.1 |
| 5,035,875 | 7/1991 | Daish | 423/580 |
| 5,100,693 | 3/1992 | Eisch et al. | 427/54.1 |
| 5,130,080 | 7/1992 | Niedrach | 376/305 |
| 5,130,081 | 7/1992 | Niedrach | 376/305 |
| 5,135,709 | 8/1992 | Andresen et al. | 376/305 |
| 5,164,152 | 11/1992 | Kim et al. | 376/305 |
| 5,321,730 | 6/1994 | Eckardt | 376/301 |

FOREIGN PATENT DOCUMENTS

| | | |
|---|---|---|
| 0265723 | 5/1988 | European Pat. Off. . |
| 0450444A1 | 10/1991 | European Pat. Off. . |
| 0526160 | 2/1993 | European Pat. Off. . |
| 0540201A1 | 5/1993 | European Pat. Off. . |
| 0651397A1 | 5/1995 | European Pat. Off. . |
| 0651073A1 | 5/1995 | European Pat. Off. . |
| 0671486A1 | 9/1995 | European Pat. Off. . |
| 2042931 | 10/1980 | United Kingdom .................. 427/595 |
| 9218665 | 10/1992 | WIPO . |

OTHER PUBLICATIONS

Derwent Publications Ltd., London, GB; AN 84–059353 & JP-A-59 016 983 (Katayama Kagaku Kogyo Kenkyush), Abstract.

Chemical Perspectives of Microelectronic Materials III Symp., Boston, MA, USA, 30 Nov. –3 Dec. 1992, 1993, Pittsburgh, PA, USA, Mater. Res. Soc. USA, pp. 353–358, Kowalczyk et al, "Characterization of Palladium Acetyl–Acetonate as a CVD Precursor for Pd Metallization."

*Primary Examiner*—Charles T. Jordan
*Assistant Examiner*—Chrisman D. Carroll
*Attorney, Agent, or Firm*—Nixon & Vanderhye

[57] ABSTRACT

A method for mitigating crack growth on the surface of stainless steel or other alloy components in a water-cooled nuclear reactor wherein a solution or suspension of a compound containing a noble metal is injected into the coolant water while the reactor is not generating nuclear heat, e.g., during shutdown or recirculation pump heatup. During shutdown, the reactor coolant water reaches temperatures as low as 120° F., in contrast to the water temperature of 550° F. during normal operation. During pump heatup, the water temperature reaches 400°–450° F. At these reduced temperatures, the rate of thermal decomposition of the injected noble metal compound is reduced. However, radiation-induced decomposition also occurs inside the reactor. In particular, the noble metal compound can be decomposed by the gamma radiation emanating from the nuclear fuel core of the reactor. The noble metal compound decomposes under reactor thermal and radiation conditions to release ions/atoms of the noble metal which incorporate in or deposit on the oxide film formed on the stainless steel and other alloy components. As a result, the electrochemical potential of the metal surface is maintained at a level below the critical potential in the presence of low levels of hydrogen to protect against intergranular stress corrosion cracking.

20 Claims, 3 Drawing Sheets

ས5,602,888

RADIATION-INDUCED PALLADIUM DOPING OF METALS TO PROTECT AGAINST STRESS CORROSION CRACKING

RELATED PATENT APPLICATIONS

This application is a continuation-in-part application of U.S. patent application Ser. No. 08/209,572 filed on Mar. 10, 1994, which in turn is a continuation-in-part application of U.S. patent application Ser. No. 08/143,513 and Ser. No. 08/143,514, now U.S. Pat. No. 5,448,605, both filed on Oct. 29, 1993.

FIELD OF THE INVENTION

This invention relates to reducing the corrosion potential of components exposed to high-temperature water. As used herein, the term "high-temperature water" means water having a temperature of about 150° C. or greater or steam. High-temperature water can be found in a variety of known apparatus, such as water deaerators, nuclear reactors, and steam-driven power plants.

BACKGROUND OF THE INVENTION

Nuclear reactors are used in electric power generation, research and propulsion. A reactor pressure vessel contains the reactor coolant, i.e. water, which removes heat from the nuclear core. Respective piping circuits carry the heated water or steam to the steam generators or turbines and carry circulated water or feedwater back to the vessel. Operating pressures and temperatures for the reactor pressure vessel are about 7 MPa and 288° C. for a boiling water reactor (BWR), and about 15 MPa and 320° C. for a pressurized water reactor (PWR). The materials used in both BWRs and PWRs must withstand various loading, environmental and radiation conditions.

Some of the materials exposed to high-temperature water include carbon steel, alloy steel, stainless steel, and nickel-based, cobalt-based and zirconium-based alloys. Despite careful selection and treatment of these materials for use in water reactors, corrosion occurs on the materials exposed to the high-temperature water. Such corrosion contributes to a variety of problems, e.g., stress corrosion cracking, crevice corrosion, erosion corrosion, sticking of pressure relief valves and buildup of the gamma radiation-emitting Co-60 isotope.

Stress corrosion cracking (SCC) is a known phenomenon occurring in reactor components, such as structural members, piping, fasteners, and welds, exposed to high-temperature water. As used herein, SCC refers to cracking propagated by static or dynamic tensile stressing in combination with corrosion at the crack tip. The reactor components are subject to a variety of stresses associated with, e.g., differences in thermal expansion, the operating pressure needed for the containment of the reactor cooling water, and other sources such as residual stress from welding, cold working and other asymmetric metal treatments. In addition, water chemistry, welding, crevice geometry, heat treatment, and radiation can increase the susceptibility of metal in a component to SCC.

It is well known that SCC occurs at higher rates when oxygen is present in the reactor water in concentrations of about 1 to 5 ppb or greater. SCC is further increased in a high radiation flux where oxidizing species, such as oxygen, hydrogen peroxide, and short-lived radicals, are produced from radiolytic decomposition of the reactor water. Such oxidizing species increase the electrochemical corrosion potential (ECP) of metals. Electrochemical corrosion is caused by a flow of electrons from anodic to cathodic areas on metallic surfaces. The ECP is a measure of the kinetic tendency for corrosion phenomena to occur, and is a fundamental parameter in determining rates of, e.g., SCC, corrosion fatigue, corrosion film thickening, and general corrosion.

In a BWR, the radiolysis of the primary water coolant in the reactor core causes the net decomposition of a small fraction of the water to the chemical products $H_2$, $H_2O_2$, $O_2$ and oxidizing and reducing radicals. For steady-state operating conditions, equilibrium concentrations of $O_2$, $H_2O_2$, and $H_2$ are established in both the water which is recirculated and the steam going to the turbine. This concentration of $O_2$, $H_2O_2$, and $H_2$ is oxidizing and results in conditions that can promote intergranular stress corrosion cracking (IGSCC) of susceptible materials of construction. One method employed to mitigate IGSCC of susceptible material is the application of hydrogen water chemistry (HWC), whereby the oxidizing nature of the BWR environment is modified to a more reducing condition. This effect is achieved by adding dissolved hydrogen to the reactor feedwater. When the hydrogen reaches the reactor vessel, it reacts with the radiolytically formed oxidizing species on metal surfaces to reform water, thereby lowering the concentration of dissolved oxidizing species in the water in the vicinity of metal surfaces. The rate of these recombination reactions is dependent on local radiation fields, water flow rates and other variables.

The injected hydrogen reduces the level of oxidizing species in the water, such as dissolved oxygen, and as a result lowers the ECP of metals in the water. However, factors such as variations in water flow rates and the time or intensity of exposure to neutron or gamma radiation result in the production of oxidizing species at different levels in different reactors. Thus, varying amounts of hydrogen have been required to reduce the level of oxidizing species sufficiently to maintain the ECP below a critical potential required for protection from IGSCC in high-temperature water. As used herein, the term "critical potential" means a corrosion potential at or below a range of values of about −230 to −300 mV based on the standard hydrogen electrode (SHE) scale. IGSCC proceeds at an accelerated rate in systems in which the ECP is above the critical potential, and at a substantially lower or zero rate in systems in which the ECP is below the critical potential. Water containing oxidizing species such as oxygen increases the ECP of metals exposed to the water above the critical potential, whereas water with little or no oxidizing species present results in an ECP below the critical potential.

It has been shown that IGSCC of Type 304 stainless steel (containing 18–20% Cr, 8–10.5% Ni, 2% Mn, remainder Fe) used in BWRs can be mitigated by reducing the ECP of the stainless steel to values below −230 mV(SHE). An effective method of achieving this objective is to use HWC. However, high hydrogen additions, e.g., of about 200 ppb or greater, that may be required to reduce the ECP below the critical potential, can result in a higher radiation level in the steam-driven turbine section from incorporation of the short-lived N-16 species in the steam. For most BWRs, the amount of hydrogen addition required to provide mitigation of IGSCC of pressure vessel internal components results in an increase in the main steam line radiation monitor by a factor of five to eight. This increase in main steam line radiation can cause high, even unacceptable, environmental dose rates that can require expensive investments in shielding and radiation exposure control. Thus, recent investigations have focused on using minimum levels of hydrogen to achieve the benefits of HWC with minimum increase in the main steam radiation dose rates.

An effective approach to achieve this goal is to either coat or alloy the alloy surface with palladium or other noble metal. Palladium doping has been shown to be effective in mitigating the crack growth rate in Type 304 stainless steel, Alloy 182 having the composition in wt.%: Ni, 59.0 min.; Cr, 13.0–17.0; Fe, 10.0 max.; Mn, 5.0–9.5; Si, 1.0 max.; Cu, 0.5 max.; Ti, 1.0 max.; S, 0.015 max.; C, 0.10 max.; P, 0.03 max.; (Nb+Ta), 1.0–2.5; other, 0.5 max., and Alloy 600 having the nominal composition in wt.%: Cr, 16.0; Fe, 8.0; Si, 0.5; Cu, 0.5 max.; Ti, 0.3 max.; C, 0.08; Ni, balance. The techniques used to date for palladium coating include electroplating, electroless plating, hyper-velocity oxy-fuel, plasma deposition and related high-vacuum techniques. Palladium alloying has been carried out using standard alloy preparation techniques. These approaches are ex-situ techniques in that they cannot be practiced while the reactor is in operation. Also noble metal coatings such as those applied by plasma spraying and by hyper-velocity oxy-fuel must be applied to all surfaces that require protection, i.e., they afford no protection to adjacent uncoated regions.

The most critical requirement for IGSCC protection of Type 304 stainless steel is to lower its ECP to values below the protection potential, i.e., −230 mV(SHE). The manner in which this potential is achieved is immaterial, e.g., by alloying, doping or by any other method. It has been demonstrated that it is sufficient to dope the oxide film by the appropriate material (e.g., Pd) to achieve a state of lower ECP in the presence of low levels of hydrogen. It was shown in later work that a thickness of 200–300 Å of the doping element (Pd) is sufficient to impart this benefit of lower potential. This is not surprising because the ECP is an interfacial property, and hence modifying the interface by a process such as doping would alter its ECP. The critical requirement is that the dopant remain on the surface over a long period of time to gain the maximum benefit from the doping action.

One method of in-situ application of a noble metal onto stainless steel or other metal surfaces inside a boiling water reactor is by injecting a decomposable noble metal compound into the high-temperature (i.e., 550° F.) water that is in contact with the metal surface during reactor operation. As a result of decomposition of the noble metal compound, the oxide film on the metal surfaces becomes doped with noble metal. The amount of noble metal dopant can be made high enough to provide sufficient catalytic activity for $H_2$ and $O_2$ recombination to reduce the ECP of the metal surfaces to required protection values. This approach of noble metal doping has been shown to be effective against crack initiation and crack growth in stainless steel at $H_2/O_2$ molar ratios greater than 2 in the reactor environment.

SUMMARY OF THE INVENTION

The present invention is an alternative method for the application of palladium or other noble metal onto stainless steel or other metal surfaces inside a boiling water reactor. The method comprises the step of injecting a solution of a compound containing a noble metal into the coolant water while the reactor is shutdown or during heatup with only recirculation pump heat, i.e., without nuclear heat generation. As used herein, the term "solution" refers to both solutions and suspensions of a noble metal compound.

During shutdown, the reactor coolant water reaches temperatures as low as 120° F., in contrast to the water temperature of 550° F. during normal operation. On the other hand, pump heat can bring the water temperature up to 400°–450° F. At these reduced temperatures, the rate of thermal decomposition of the injected noble metal compound is reduced. However, decomposition of the noble metal compound is also induced by radiation produced inside the reactor. In particular, the noble metal compound can be decomposed by the gamma radiation emanating from the nuclear fuel core of the reactor. Decomposition can also be precipitated by radiation from radioactive isotopes in the material of the reactor component to be protected by noble metal doping. Thus the noble metal compound decomposes under reactor thermal and radiation conditions to release atoms of the noble metal which incorporate in or deposit on the oxide film formed on the stainless steel and other alloy components. As used herein, the term "atoms" also includes ions of the noble metal.

The preferred compound for use in noble metal doping is palladium acetylacetonate. The concentration of palladium in the reactor water is preferably in the range of 5 to 100 ppb. Upon injection, the palladium acetylacetonate decomposes and deposits palladium on the crudded (heavily oxidized) stainless steel and other alloy surfaces immersed in the water. The palladium is incorporated into the oxide film or crud via a process wherein palladium ions/atoms apparently replace iron, nickel and/or chromium atoms in the oxide film or crud, resulting in palladium doping. Alternatively, palladium may be deposited within or on the surface of the oxide film or crud in the form of a finely divided metal. The oxide film is believed to include mixed nickel, iron and chromium oxides.

The passive oxide films on the surfaces of structural materials can be doped or coated with palladium or other noble metal using either in situ or ex situ techniques. In accordance with both techniques, the structural material is immersed in a solution or suspension of a compound containing the noble metal. Decomposition of the noble metal compound in the solution is then induced by exposing the immersed material to electromagnetic radiation, e.g., ultraviolet or gamma radiation. Even at the low temperatures reached during reactor shutdown or during heatup with recirculation pump heat, the radiation-induced decomposition in combination with thermal decomposition provide noble metal doping of oxide film or crud sufficient to reduce the ECP at the oxide film/water interface to below the critical threshold potential, thereby mitigating stress corrosion cracking.

DETAILED DESCRIPTION OF THE PREFERRED EMBODIMENTS

Figure 1:
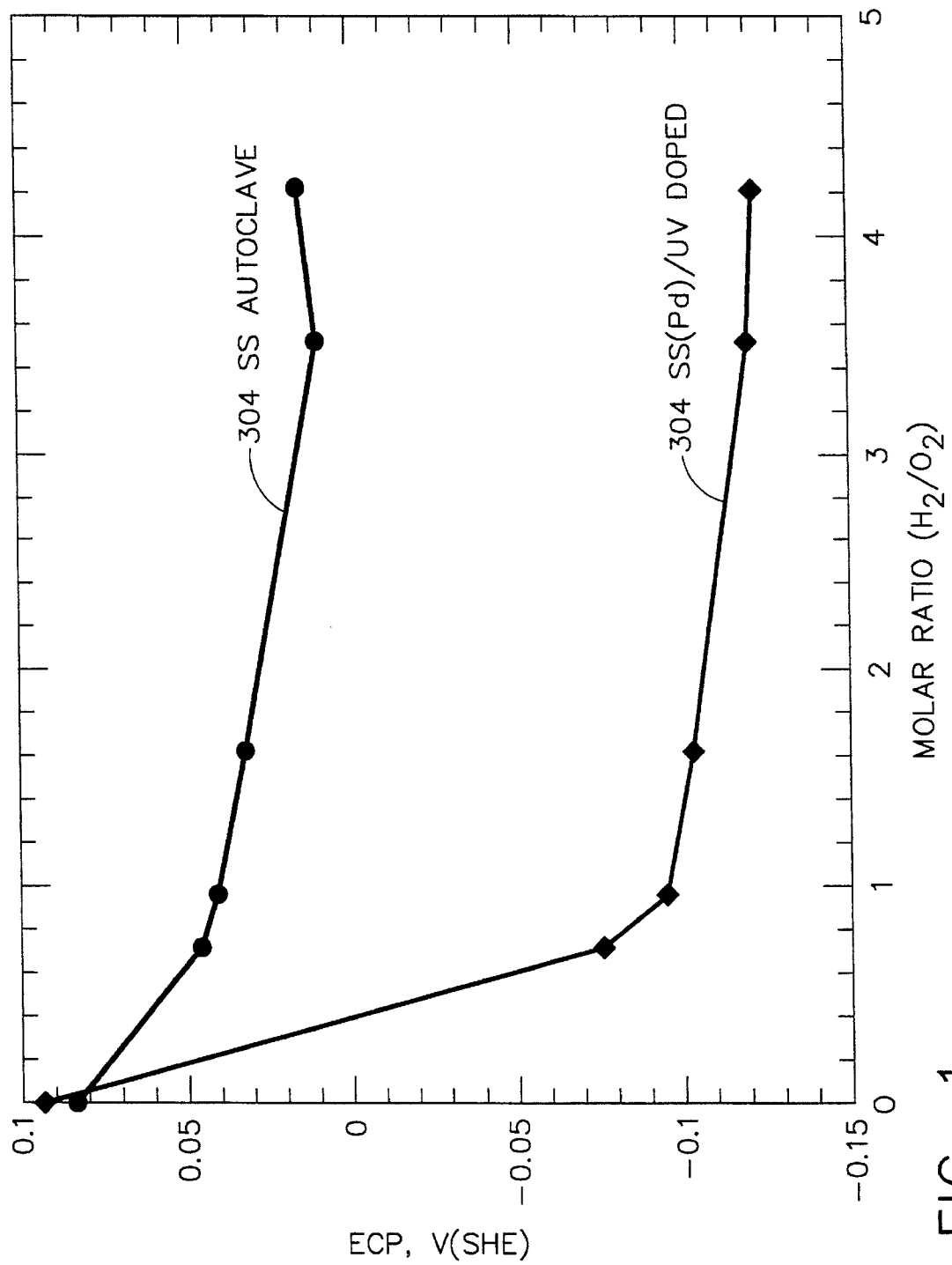
FIG. 1 is a plot showing the ECP response as a function of the molar ratio of hydrogen to oxygen for a Pd-doped Type 304 stainless steel specimen wherein palladium doping was induced by exposure to ultraviolet radiation at a temperature of 78° F. (♦) and for a Type 304 stainless steel autoclave which had no palladium doping (●).

The present invention is an in situ technique to coat or dope the oxide film or crud formed on metal surfaces of reactor components with noble metal while the reactor is shutdown or during heatup with recirculation pump heat only, i.e., without nuclear heat generation. The noble metal is brought into contact with the oxide layer by injecting a noble metal-containing compound into the coolant water during an outage or during pump heatup. Preferably the noble metal compound is injected at a point upstream of the feedwater inlet.

While the rate of thermal decomposition of the noble metal compound during shutdown is diminished relative to the decomposition rate at the operating temperature of the reactor, the gamma and neutron radiation in the reactor core act to decompose the compound even during shutdown. This decomposition frees noble metal ions/atoms for deposition on or incorporation in the oxide film or crud on reactor components which have been in service for an extended period of time.

The preferred embodiment of the present invention involves radiation-induced palladium doping of reactor components performed at ambient temperature or heatup temperatures lower than the operating temperature of 550° F. The radiation-induced doping causes deposition/doping of the reactor component surfaces with palladium in an amount that provides catalytic activity for $H_2$ and $O_2$ recombination sufficient to reduce the ECP of stainless steel and other alloy surfaces to required levels for protection against intergranular stress corrosion cracking.

Radiation-induced palladium doping was tested with a Type 304 stainless steel surface using ultraviolet (UV) radiation. A Type 304 stainless steel constant extension rate tensile (CERT) specimen (preoxidized) was immersed in a well-stirred solution of palladium acetylacetonate ($Pd(CH_3COCHCOCH_3)_2$). The palladium acetylacetonate solution was prepared by dissolving/suspending 43 mg of palladium acetylacetonate in 20 ml of ethanol and diluting the resulting mixture to one liter with deionized water. The solution was vigorously mixed to obtain a uniform distribution of the compound. The mixture so prepared had a palladium content of 15 mg/liter (15 ppm) as palladium. This stock solution was diluted to obtain a 100 ppb Pd solution. After immersing the CERT specimen in the palladium acetylacetonate solution, a UV lamp was also immersed in the same solution so that the distance of separation between the UV lamp and the CERT specimen was approximately 1 cm. The temperature of the solution was 78° F. After a 10-min exposure of one side of the specimen to UV radiation, the lamp was moved to the other side, exposing that side to another 10 min of UV radiation to obtain a uniform doping of the CERT specimen with palladium. After radiation treatment, the specimen was washed well with deionized water and then tested at 550° F. for its ECP response as a function of the molar ratio of $H_2/O_2$ in the high-purity water environment being tested.

The results of this study are shown in FIG. 1. Clearly, the ECP of the specimen responded to hydrogen better than the Type 304 stainless steel autoclave without palladium, showing the presence of palladium on the UV-treated specimen. The response was not as good as thermal doping, e.g., at a temperature of 550° F., presumably due to a lower palladium content on the surface.

The present invention is not limited to UV radiation. Any form of electromagnetic radiation, including visible light or higher-energy radiation such as gamma radiation, is expected to provide doping. The extent of doping, however, is expected to depend on the energy of the ionizing radiation and the exposure time. Higher-energy radiation assists in doping the surface with palladium faster and more effectively. For example, experiments have proven that gamma radiation is effective in causing palladium doping of surfaces. The results of experiments involving gamma-assisted palladium doping are shown in FIG. 2.

Figure 2:
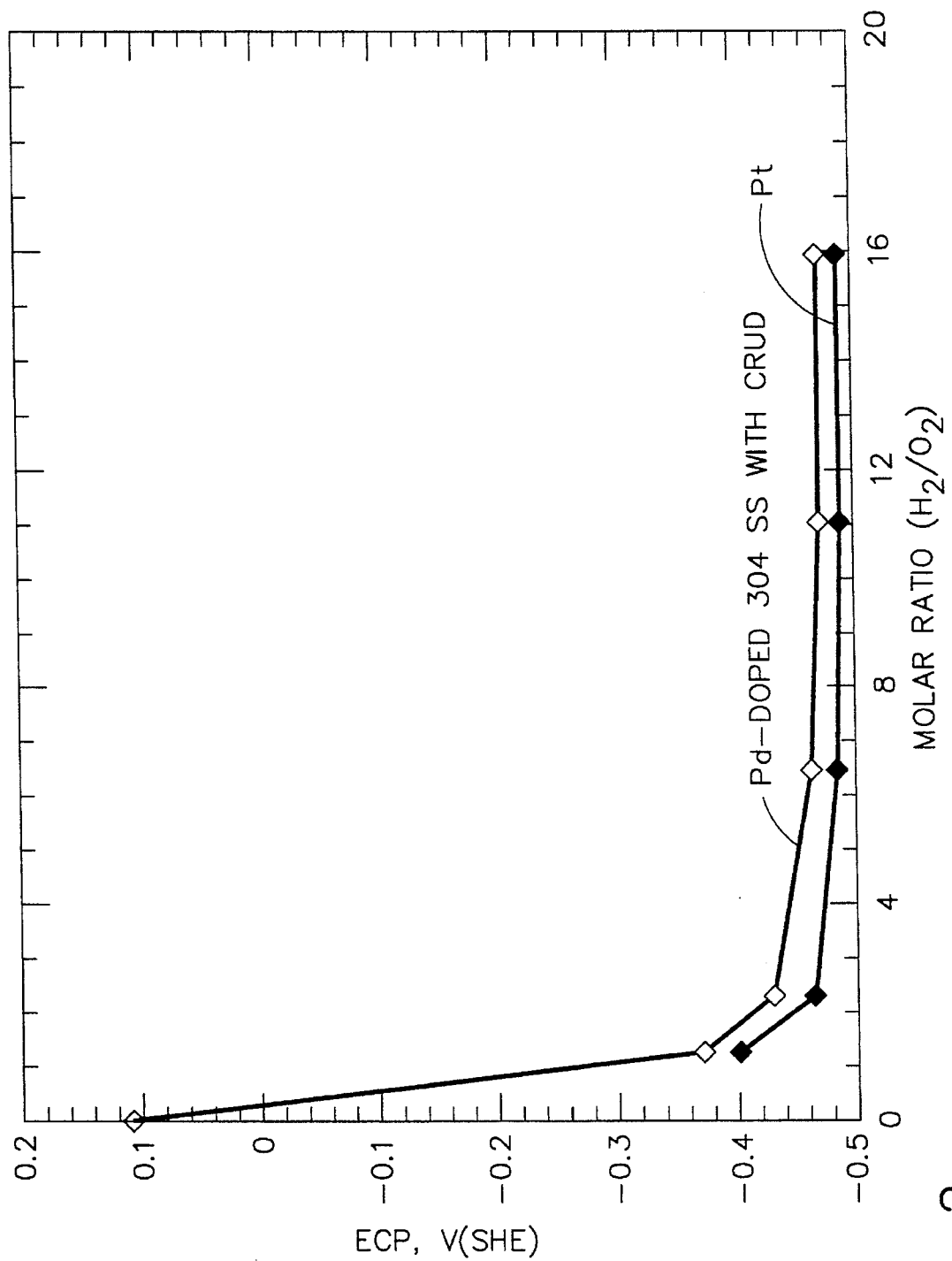
FIG. 2 is a plot showing the ECP response as a function of the molar ratio of hydrogen to oxygen for an in-reactor crud-deposited Type 304 stainless steel specimen which had an inherent radiation level of 50–60 mRad/hr and was subsequently doped with palladium in 100 ppb Pd at 200° F. for 24 hr (◊) and for a pure platinum specimen (♦) for comparison.

In FIG. 2, one curve shows the ECP response of pure platinum and the other curve shows the ECP response of a Type 304 stainless steel specimen (Type 304 stainless steel/crud/palladium) that had been in a reactor for 10 years. The Type 304 stainless steel specimen was believed to have a truly representative oxide layer (or crud) of thickness 1–2 µm on its surface because of its lengthy immersion in reactor water. After being removed from the reactor, the crudded Type 304 stainless steel specimen was palladium doped (100 ppb Pd at 200° F. for 24 hr) in a hot cell facility.

The purpose of this gamma-assisted palladium doping test was to determine the effects of gamma radiation (inherent on the specimen due to activation) and moderately high temperature (200° F.) on the palladium doping process, which may be used to coat or dope reactor internals with palladium or other noble metal. Another objective of the test was to determine the effectiveness of palladium doping on a crud-deposited surface. The test involved the following steps.

In Step I, a specimen was cut from surveillance basket material (Type 304 stainless steel) which had been in the mid-core region of a boiling water reactor for 10 years in the expectation that the material would have a representative crud layer on its surface. The presence of crud was confirmed by analysis as well as by measuring the thickness (1–2 µm) using scanning electron microscopy. Therefore, machining was done so as to minimize any crud spalling. The specimen was cut so that a minimum number of cutting edges were generated. The specimen dimensions were approximately 1 cm×2 cm.

In Step II, a stainless steel wire was spot-welded to the specimen. The amount of cleaning required for the spot welding process was minimized. This specimen was then immersed in a 100 ml aqueous solution of palladium acetylacetonate (100 ppb as palladium) containing 0.01% ethyl alcohol. The solution was stirred and heated to 200° F. in a flask fitted with a reflux condenser over a period of about one day. After the test, the specimen was removed from the flask, washed and set aside for the ECP test in Step III.

In Step III, the specimen from Step II was installed inside an autoclave attached to a recirculating flow system containing high-purity water. An ECP test of the specimen was performed at 550° F. at $H_2/O_2$ molar ratios ranging from 0.5 to about 5. The total test time was one week.

The results of these experiments are plotted as open diamonds in FIG. 2. These results are compared with experimental data showing the ECP response of pure platinum. The following conclusions can be drawn from FIG. 2. First, the ECP response, at 550° F., of the palladium-doped crud-coated Type 304 stainless steel specimen was very similar to that of pure platinum. Second, palladium doping is feasible on heavily oxidized (crudded) surfaces, which is desirable for in-reactor application. Third, it is possible to perform palladium doping at temperatures, e.g., 200° F., below the temperature of an operating boiling water reactor, which is typically at least 550° F., due to the high radiation levels present in the reactor, even during an outage.

Figure 3:
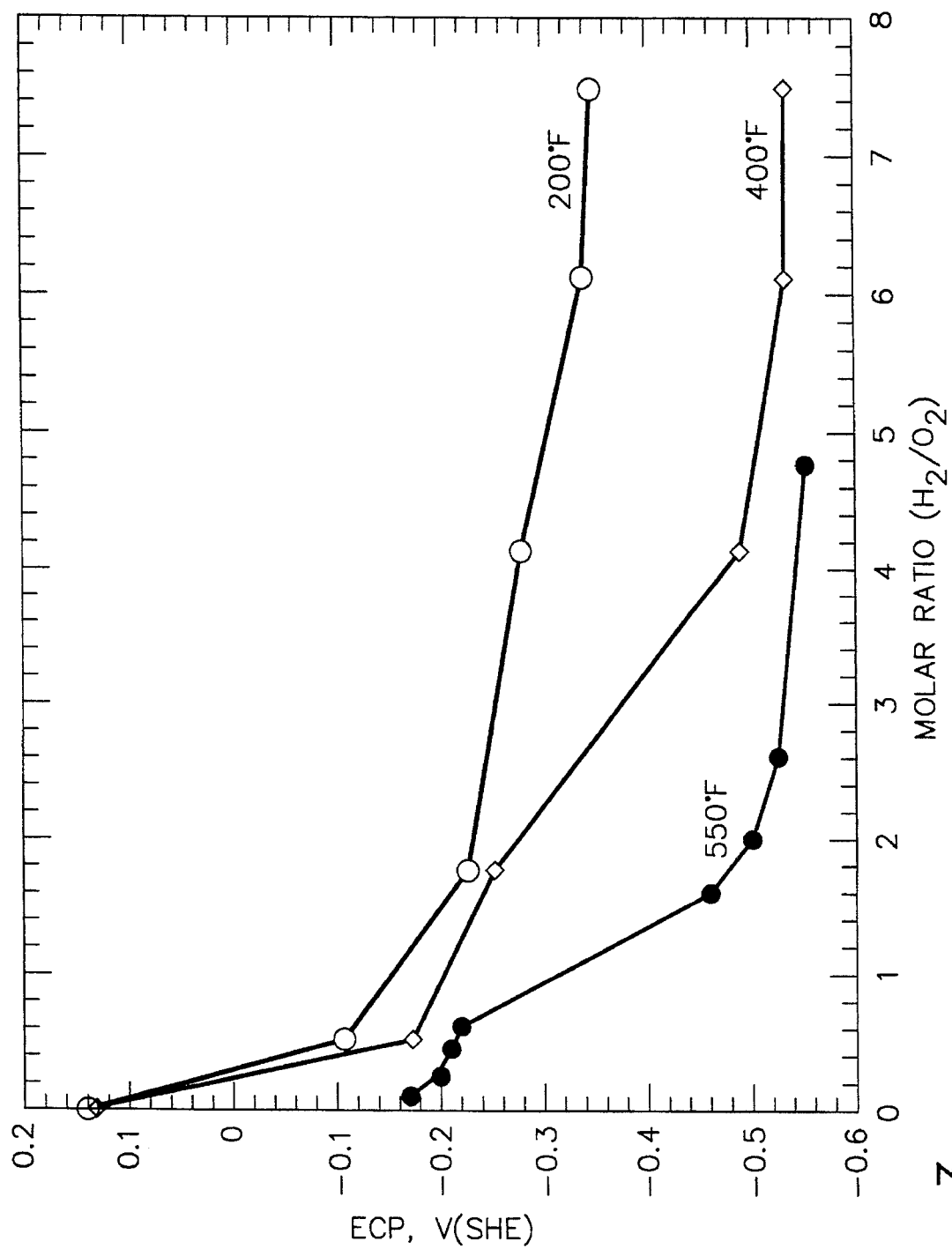
FIG. 3 is a plot showing the ECP response as a function of the molar ratio of hydrogen to oxygen for three Pd-doped Type 304 stainless steel specimens doped with palladium at three different temperatures: (o) 200° F.; (◊) 400° F.; and (●) 550° F.

FIG. 3 shows the influence of palladium doping temperature on the ECP response in the absence of radiation. Type 304 stainless steel specimens were doped with palladium at temperatures of 200° F., 400° F. and 550° F. at different $H_2/O_2$ molar ratios ranging from 0 to about 7.5. The doping done at 200° F. without any radiation influence showed that the lowest ECP reached at a $H_2/O_2$ molar ratio of 7 was approximately −0.330 V(SHE). The data in FIG. 3 show that, in the absence of electromagnetic radiation, palladium doping is more effective when performed at higher temperatures.

In contrast, as seen in FIG. 2, with gamma radiation assisting the doping process, the ECP reached at a $H_2/O_2$ molar ratio of 7 decreased to almost −0.460 V(SHE), i,e, a benefit of 160 mV at a much lower doping temperature of 200° F. In particular, it is believed that the radioactivity of this crudded specimen contributed to an increase in the rate at which the palladium acetylacetonate in the coolant water decomposed during palladium doping. Thus, the good ECP response of the crudded specimen taken from a reactor was attributable to radiation-assisted palladium doping of the specimen.

In the foregoing experiment, the radiation in aid of noble metal doping was inherent, i.e., was emitted by radioisotopes (due to activation as a result of reactor exposure) contained in the material of the specimen. Specifically, the crudded Type 304 stainless steel (reactor exposed) specimen had an inherent radiation dose of 50 to 60 mRad/hr, because of its exposure to reactor water over a period of 10 years. It follows that the rate at which palladium acetylacetonate decomposes inside a boiling water reactor will be increased dramatically due to the effect of gamma radiation emitted by the nuclear fuel core. The contribution to the decomposition rate made by electromagnetic radiation will allow palladium doping of equal effect to be achieved at relatively lower doping temperatures.

The main conclusions to be drawn from the foregoing experimental data are as follows: (1) gamma radiation assists the palladium doping process; (2) the presence of gamma radiation facilitates palladium doping at a lower temperature than the temperature at which thermal doping is performed (i.e., approximately 550° F.); and (3) palladium doping of in-reactor surfaces (crudded) is possible.

A significant advantage of gamma-induced doping is that when thermal doping is practiced in nuclear reactor applications, gamma radiation would inherently be present even if the reactor is in an outage, thereby providing an additional benefit of radiation-induced palladium doping of surfaces. Thus, when thermal doping of palladium is practiced in nuclear reactors, the doping will be due to a combined effect of both thermally induced as well as radiation-induced effects.

The foregoing method has been disclosed for the purpose of illustration. Variations and modifications of the disclosed method will be readily apparent to practitioners skilled in the art of reactor kinetics. For example, the noble metals which can be applied using this technique include palladium, platinum, ruthenium, rhodium, osmium, iridium, and mixtures thereof. The noble metal can be injected in the form of an organic or organometallic compound to reduce the potential of reactor components made of stainless steel or other alloys even in the absence of hydrogen injection. Alternatively, the noble metal can be injected in the form of an inorganic compound in conjunction with hydrogen injection to reduce the ECP at the surface of reactor components. All such variations and modifications are intended to be encompassed by the claims set forth hereinafter.

We claim:

1. A method for mitigating stress corrosion cracking in an oxided metal component in a water-cooled nuclear reactor, comprising the steps of:

injecting a solution of a compound containing a noble metal into the coolant water during reactor shutdown or during heat-up with recirculation pump heat only; and causing said noble metal compound to decompose under reactor radiation conditions to release atoms of said noble metal which incorporate in said oxided metal component.

2. The method as defined in claim 1, wherein exposing said noble metal compound to gamma radiation induces decomposition.

3. The method as defined in claim 1, wherein said noble metal is palladium.

4. The method as defined in claim 3, wherein said compound is an organometallic compound of palladium.

5. The method as defined in claim 4, wherein said organometallic compound is palladium acetylacetonate.

6. The method as defined in claim 1, wherein said metal component is made of stainless steel.

7. The method as defined in claim 1, wherein said metal component is made of nickel-based alloy.

8. A method of doping an oxided metal component with a noble metal, comprising the steps of:

immersing the oxided metal component in water;

adding a noble metal compound to the water; and exposing the oxided metal component in water to electromagnetic radiation to cause noble metal compound in the vicinity of the oxide and metal component to decompose to release atoms of said noble metal which incorporate in said oxided metal component.

9. The method as defined in claim 8, wherein said electromagnetic radiation is gamma radiation.

10. The method as defined in claim 8, wherein said electromagnetic radiation is ultraviolet radiation.

11. The method as defined in claim 8, wherein said noble metal is palladium.

12. The method as defined in claim 11, wherein said compound is an organometallic compound of palladium.

13. The method as defined in claim 12, wherein said organometallic compound is palladium acetylacetonate.

14. The method as defined in claim 8, wherein said metal component is made of stainless steel.

15. The method as defined in claim 8, wherein said metal component is made of nickel-based alloy.

16. The method as defined in claim 8, wherein said metal component is a component immersed in the coolant water of a nuclear reactor and said noble metal compound is added to said coolant water.

17. A method for mitigating stress corrosion cracking in a metal component in a water-cooled nuclear reactor, comprising the steps of:

injecting a solution of a compound containing a noble metal into the coolant water when said coolant water has a temperature less than the operating temperature of the reactor; and causing said noble metal compound to decompose under reactor radiation and thermal conditions to release atoms of said noble metal which incorporate in an oxide layer on said metal component.

18. The method as defined in claim 17, wherein said noble metal is palladium.

19. The method as defined in claim 17, wherein said noble metal compound is palladium acetylacetonate.

20. The method as defined in claim 17, wherein said metal component is made of stainless steel.

* * * * *